United States Patent
Lange et al.

(12)

(10) Patent No.: US 6,479,557 B1
(45) Date of Patent: Nov. 12, 2002

(54) PROCESS FOR THE PREPARATION OF HYDROCARBONS FROM CARBON MONOXIDE AND HYDROGEN

(75) Inventors: Jean-Paul Lange, Amsterdam (NL); Ian Ernest Maxwell, Amsterdam (NL); Bob Scheffer, Grand Couronne (FR)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 09/504,665

(22) Filed: Feb. 14, 2000

(30) Foreign Application Priority Data

Feb. 15, 1999 (EP) .............................. 99301099

(51) Int. Cl.[7] .......................... C07C 27/00; C07C 27/06
(52) U.S. Cl. ...................... 518/706; 518/700; 518/707; 518/728
(58) Field of Search ................................ 518/700, 706, 518/707, 728

(56) References Cited

U.S. PATENT DOCUMENTS 4,624,968 A 11/1986 Kim et al. .................. 518/707

FOREIGN PATENT DOCUMENTS

| EP | 0147696 | A2 | 12/1984 | .......... H01G/13/00 |
|---|---|---|---|---|
| EP | 0153781 | A2 | 2/1985 | ............. C07C/1/04 |
| EP | 0168892 | A2 | 7/1985 | ............. C01B/3/32 |
| EP | 0174696 | A1 | 9/1985 | ............. C07C/1/04 |
| EP | 0178007 | A2 | 9/1985 | ............. C01B/3/36 |
| EP | 0428223 | A1 | 11/1990 | ............. B01J/21/06 |
| EP | 0510771 | A1 | 4/1992 | ............. B01J/37/00 |
| EP | 0679620 | A2 | 4/1995 | |
| GB | 2092172 | A | 12/1981 | ............. C07C/1/04 |
| GB | 2243616 | A | 5/1990 | ............. C07C/1/04 |

OTHER PUBLICATIONS

"Higher Alcohol Synthesis," by Pio Forzatti, Enrico Tronconi, and Italo Pasquon, *Catal. Rev.—Sci. Eng.*, 33(1&2), pp. 109–168 (1991).

*Primary Examiner*—Jafar Parsa

(57) ABSTRACT

A process for the preparation of at least two organic products from a synthesis gas by
 (i) converting a first synthesis gas feed to a first organic product and a first by-product;
 (ii) converting a second synthesis gas feed to a second organic product and a second by-product;
 (iii) separating the first and/or second by-product from, respectively, the first and/or second organic product, and
 (iv) mixing the separated first and/or second by-product with, respectively, the second and/or first organic product.

Preferably, the first organic product is paraffinic hydrocarbons or oxygenates and the second organic product is olefinic hydrocarbons or oxygenates.

20 Claims, No Drawings

PROCESS FOR THE PREPARATION OF HYDROCARBONS FROM CARBON MONOXIDE AND HYDROGEN

The present invention relates to a process for the preparation of hydrocarbons from a mixture of carbon monoxide and hydrogen. The present invention relates in particular to a process for the preparation of hydrocarbons from a mixture of carbon monoxide and hydrogen having a given $H_2/CO$ molar ratio.

Mixtures of hydrogen and carbon monoxide are often referred to as synthesis gas. Such synthesis gas can be used in numerous well-known processes to produce a large variety of organic compounds, containing carbon, hydrogen and, optionally, oxygen moieties.

A process for the preparation of paraffinic hydrocarbons from a mixture of carbon monoxide and hydrogen (syngas) is commonly known as Fischer-Tropsch synthesis. This synthesis process involves contacting syngas at elevated temperature and pressure with a catalyst, comprising as catalytically active component a Group VIII metal, in particular Fe, Ni, Ru or Co, to yield paraffinic hydrocarbons. A detailed description of an example of such a Fischer-Tropsch synthesis process can be found in EP-A-0428223 and EP-A-0174696.

The Fischer-Tropsch synthesis process referred to hereinabove, in particular a process using a catalyst comprising Ni, Ru or Co, and having no Co-shift activity, typically consumes syngas at a $H_2/CO$ molar usage ratio of 2.0 to 3.0, in particular 2.0 to 2.3, mainly depending on the length of the paraffinic hydrocarbons formed. It will be understood that when a given Fischer-Tropsch synthesis process consumes syngas at a $H_2/CO$ molar usage ratio of for example 2.1, the $H_2/CO$ molar feed ratio should preferably be 2.1 as well in order to avoid a surplus of either $H_2$ or CO.

A problem underlying the present invention is that a syngas feed having a $H_2/CO$ molar ratio of 2.1 is not readily available and can only be prepared at unacceptably high costs.

In the art a number of processes are known to prepare syngas. Depending on the process for preparing syngas and the type of organic feed to such processes, the $H_2/CO$ molar ratio of the syngas may vary widely. If coal is used as organic feed in such a process, the $H_2/CO$ molar ratio of the resulting syngas is generally lower than if natural gas is used as organic feed. A steam methane reforming process, using natural gas as organic feed, typically produces syngas having a $H_2/CO$ molar ratio of at least 3. A process involving partial oxidation, either autothermal or catalytic, of natural gas typically produces syngas having a $H_2/CO$ molar ratio of 1.7. A partial oxidation process using coal or residual oil as organic feed typically produces syngas having a $H_2/CO$ molar ratio of 0.5.

Accordingly, in order to obtain a syngas having a $H_2/CO$ molar ratio of for example 2.1, one has to prepare syngas using at least two different processes, such as a combination of steam methane reforming and partial oxidation of natural gas, and mix the two $H_2/CO$ mixtures thus obtained. For example EP-A-0168892 and EP-A-0178007 disclose energy efficient methods to prepare syngas from two different processes. Alternatively, one could prepare syngas by one syngas preparation process and mix the syngas thus prepared with a separate hydrogen or carbon monoxide stream to arrive at the desired hydrogen to carbon monoxide ratio.

It will be understood that it will be most desirable to be able to use a syngas feed in a synthesis process, which syngas feed is obtained from one syngas preparation process only, without the need to mix the syngas feed with another syngas having a different hydrogen to carbon monoxide ratio or separate hydrogen or carbon monoxide streams.

GB-A-2243616 discloses a process for the production of paraffinic and aromatic hydrocarbons from a carbonaceous feedstock. This process involves converting the carbonaceous feedstock into synthesis gas having a $H_2/CO$ molar ratio of less than 2.1, converting the synthesis gas partially into paraffinic hydrocarbons and converting the remaining synthesis gas into aromatic hydrocarbons. The process for the preparation of paraffinic hydrocarbons consumes synthesis gas at a $H_2/CO$ usage ratio higher than the $H_2/CO$ feed ratio, whereas the process for the preparation of aromatic hydrocarbons consumes synthesis gas at a $H_2/CO$ usage ratio lower than the $H_2/CO$ feed ratio. As outlined in this document the most efficient conversion is obtained when the overall $H_2/CO$ usage ratio is the same as the $H_2/CO$ feed ratio.

Examples of other well-known processes for the preparation of organic products from synthesis gas are processes for the preparation of oxygen-containing hydrocarbons like methanol, higher alcohols or dimethylether and are well known in the art.

GB-A-2092172 discloses a process for the preparation in a first step, of oxygen-containing organic compounds from synthesis gas having a $H_2/CO$ molar ratio of at least 0.5, and, in a second step, paraffinic hydrocarbons from unconverted synthesis gas from the first step. The oxygen-containing compounds obtained in the first step can be used as intermediates in the production of other organic compounds like olefins.

The preparation of olefins directly from synthesis gas is well known to those skilled in the art. U.S. Pat. No. 4,518,707 and EP-A-0446035 disclose examples of such preparation process.

U.S. Pat. No. 4,624,968 discloses a multi-stage Fischer-Tropsch process for the production of paraffinic waxes by converting in a first step synthesis gas into olefins, and converting in a second step the olefins and any additional synthesis gas into paraffins. The two steps may be combined into one step by using a mixture of the required different catalysts in one catalyst bed. This two-stage arrangement for the preparation of paraffinic hydrocarbons is said to offer the advantage that it results in increased amounts of heavy hydrocarbons and lower selectivities for methane and ethane as compared with the production of paraffins in one step.

One of the problems with processes using synthesis gas as feed is the production of by-products. EP-A-0153781 discloses a two-step process for the preparation of paraffinic hydrocarbons. In the first step a catalyst is used which is capable of yielding a product containing only limited amounts of by-products. Nevertheless, by-products are present in the product of this process. The formation of by-products becomes an even more important problem if it is desired to prepare organic products for use in the chemical industry. For example, if it is desired to produce olefinic hydrocarbons, the formation of paraffinic hydrocarbons represents a problem.

By-products can be separated from the desired product by means known in the art, such as by molecular sieves, adsorption, distillation or washing, but this is relatively expensive and is often not economically viable in view of the limited volumes of by-products produced (that is, no economy-of-scale).

It would be desirable if by-products of a synthesis process, using a synthesis gas feed, could be separated from the main product and used in an economically viable way.

As with the separation of by-products, the production of organic products from synthesis gas is also governed by the economy-of-scale. Thus, preferably, the production of organic products from synthesis gas is carried out on a large scale. However, if it is desired to prepare organic products for use in the chemical industry, the market could be relatively small as compared with the scale required to make preparation of those organic products economically viable, thus prohibiting the economic production of those products.

Despite the maturity of research in this field and despite the wealth of publications that are published each year in this field, it is believed that no one has considered to prepare in a first step a first organic product and a first by-product, and prepare in a second step a second organic product and a second by-product, and in a third step, e.g. separate the first by-product from the first organic product and mix the first by-product with the product from the second step.

The present invention therefore provides a process for the preparation of at least two organic products from synthesis gas by (i) converting a first synthesis gas feed to a first organic product and a first by-product;

(ii) converting a second synthesis gas feed to a second organic product and a second by-product;

(iii) separating the first and/or second by-product from, respectively, the first and/or second organic product, and (iv) mixing the first and/or second by-product with, respectively, the second and/or first organic product.

It will be understood that this is particularly advantageous where the value of the first or second by-product is higher in a mixture with respectively the second or first organic product than vice versa. An example is where e.g. the first by-product forms a starting mixture with the second organic product for further processing.

Preferably, the process comprises in step (iii), separating both the first and second by-product from, respectively, the first and second organic product. More preferably the process further comprises in step (iv), mixing the first and second by-product with, respectively, the second and first organic product.

It will be appreciated that it is most advantageous if the first by-product has the same general structural formula as the second organic product. Also, it is most advantageous if the second by-product has the same general structural formula as the first organic product. Whereas for the individual by-products the amounts produced could be too low to warrant commercial exploitation, in particular in isolated parts of the world, the by-product mixed with a main product, that is the first or second organic product, could very well warrant commercial exploitation.

Typically, the general structural formulae of the first and second organic products are independently chosen from the groups classified as olefins, paraffins, alkanols, aldehydes or ketones.

In a further embodiment of the present invention, the process is carried out such that substantially all synthesis gas is consumed and no hydrogen or carbon monoxide is left over. In a further aspect, the hydrogen to carbon monoxide usage ratio of the conversion from synthesis gas to the first organic product is higher than the feed ratio of the synthesis gas, whereas the usage ratio of the conversion to the second organic product is lower than the feed ratio of the synthesis gas.

Accordingly, the present invention further provides a process for the preparation of at least two organic products from a synthesis gas, wherein the synthesis gas, comprising a mixture of hydrogen and carbon monoxide, has a molar ratio of hydrogen to carbon monoxide F, which process comprises effecting in a first stage one of the following procedures:

(a) converting a first synthesis gas feed to a first organic product and a first by-product under conditions of a carbon monoxide conversion of $X_i$ and a molar usage ratio of hydrogen to carbon monoxide of $F_i$, wherein $F_i$ is greater than F; or (b) converting a second synthesis gas feed to a second organic product and a second by-product under conditions of a carbon monoxide conversion of $X_{ii}$ and a molar usage ratio of hydrogen to carbon monoxide of $F_{ii}$, wherein $F_{ii}$ is less than F;

and supplying the unconverted carbon monoxide and hydrogen to a second stage in which the other of procedure (a) or (b) is effected; the first and second stages being effected under such conditions that the following relationship is met:

$$F = X_i \cdot F_i + X_{ii} \cdot F_{ii} + c \qquad (I)$$

wherein c is up to 0.2. Preferably, c is up to 0.1. Most preferably c equals zero. Incidentally, c may be slightly negative, that is down to −0.1 due to a CO-shift reaction in the first and/or second stage. The molar usage ratio of a CO-shift reaction ($CO + H_2O \rightarrow CO_2 + H_2$) is −1. It is to be understood that negative values down to −0.1 are included within the meaning of the terms up to 0.2 and up to 0.1, as referred to hereinabove.

It is to be understood that $X_i$ and $X_{ii}$ represent an overall carbon monoxide conversion based on the carbon monoxide present in the synthesis gas. Thus, the carbon monoxide conversion $X_i$ is calculated by dividing the total amount of carbon monoxide converted in the first synthesis process, that is the process for the preparation of the first organic product, by the total amount of carbon monoxide originally present in the synthesis gas. The conversions $X_i$ and $X_{ii}$ are not necessarily the same as the conversions per pass. The conversion per pass may for example be lower due to recycle loops of synthesis gas having a different hydrogen to carbon monoxide molar ratio.

Accordingly, it will be appreciated that the $H_2/CO$ molar ratio of the first or second synthesis gas feed is not necessarily the same as the $H_2/CO$ molar ratio of the synthesis gas produced in the synthesis gas production process. For example the $H_2/CO$ molar ratio of the first or second synthesis gas feed may have been altered by any unconverted synthesis gas recycle streams. As will be described hereinafter, in the preparation of paraffinic hydrocarbons from synthesis gas it may be preferred to use a synthesis gas feed having a $H_2/CO$ molar ratio which is significantly lower than the usage ratio of the synthesis process. In a preferred embodiment of the invention, at least part of the unconverted carbon monoxide and hydrogen of procedure (a) or (b) is the only synthesis gas feed for the other procedure.

The process as described hereinabove is preferably carried out using as starting material a synthesis gas having a molar ratio of hydrogen to carbon monoxide F of less than 2.1. In a preferred embodiment the synthesis gas is prepared from natural gas by a catalytic or autothermal partial oxidation process, which processes are known in the art. This has the advantage that a synthesis gas is produced having a $H_2/CO$ molar ratio in the range of from 1.5 to 1.9. This is particularly beneficial if it is desired to produce large amounts of a first product having a $H_2/CO$ usage ratio relatively close to the molar ratio of the synthesis gas, for example paraffinic hydrocarbons, in one step and to produce in a second step smaller amounts of products to be used as chemical feedstock and having a $H_2/CO$ usage ratio relatively far from the molar ratio of the synthesis gas. Examples of such products to be used as chemical feedstock are olefins and oxygen-containing products. Accordingly, in a preferred embodiment of the present invention a synthesis gas is used having a molar ratio of hydrogen to carbon monoxide F in the range of from 1.5 to 1.9, in particular about 1.7.

Typically, the first synthesis gas feed is converted to paraffinic hydrocarbons as first organic product. The conversion is typically carried out using a so-called Fischer-Tropsch catalyst containing a Group VIII metal. Fischer-Tropsch catalysts are well known to those skilled in the art. Examples of suitable Fischer-Tropsch catalysts, selective for the conversion of synthesis gas to paraffinic hydrocarbons are those containing cobalt or ruthenium as active metal, in particular those described in EP-A-0428223 and EP-A-0510771.

The molar synthesis gas usage ratio $F_i$ of this conversion typically lies in the range of from 2.0 to 2.3, in particular 2.1. Yet, it has been found advantageous to use a synthesis gas feed to the process having a hydrogen to carbon monoxide molar ratio in the range of from 0.6 to 1.4, in particular 1.1. The use of a synthesis gas feed which has a significantly lower hydrogen to carbon monoxide ratio than the actual usage ratio is particularly beneficial for the selectivity of the process to long-chain paraffinic hydrocarbons. A disadvantage is that the use of such feed results in larger by-products production. Typically, the process for the conversion of synthesis gas feed to paraffinic hydrocarbons produces olefins and/or oxygenates as by-products.

Accordingly in one aspect of the present invention, the first synthesis gas feed is converted to paraffinic hydrocarbons as first organic product and oxygenates and/or olefinic hydrocarbons as first by-product.

Reaction conditions for preparation of paraffinic hydrocarbons from synthesis gas may vary widely. Typically, the preparation of paraffinic hydrocarbons is carried out at a temperature in the range of from 100 to 400° C., in particular from 200 to 250° C. The total pressure may be chosen from 0.1 to 10 MPa, in particular from 2 to 6 MPa. The Gas Hourly Space Velocity (GHSV) typically may be chosen from 100 to 10000 Nl/l/h, preferably from 500 to 2000 Nl/l/h. Preferably the reaction conditions are such that, with a given catalyst, the conversion $X_i$ is such that formula I is met. The determination of such reaction conditions belongs to the ordinary skills of a person skilled in the art.

In one embodiment, the second synthesis gas feed is converted to olefinic hydrocarbons, in particular as second organic product. The conversion is typically carried out using an olefin synthesis catalyst. Olefin synthesis catalysts are well known to those skilled in the art. Examples of suitable olefin synthesis catalysts are those containing a group VIII metal, for example iron, optionally in combination with an alkali metal such as potassium and/or optionally a metal chosen from the transition metals, in particular groups Ib, IIb, Vb, VIb, VIIb or VIII of the Periodic Table of the Elements as published in the Handbook of Chemistry and Physics 65th edition, preferably manganese or zinc. Optionally, the catalytically active metals are supported on a carrier, typically a refractory oxide carrier. By-products that may be produced in this process comprise oxygenates and/or paraffinic hydrocarbons.

Accordingly, in a further aspect of the present invention the second synthesis gas feed is converted to olefinic hydrocarbons as second organic product and oxygenates and/or paraffinic hydrocarbons as second by-product.

Reaction conditions for preparation of olefinic hydrocarbons from synthesis gas may vary widely. Typically, the preparation of olefinic hydrocarbons is carried out at a temperature in the range of from 100 to 400° C., in particular from 250 to 300° C. The total pressure may be chosen from 0.1 to 10 MPa, in particular from 0.5 to 4 MPa. The Gas Hourly Space Velocity (GHSV) typically may be chosen from 100 to 10000 Nl/l/h, preferably from 500 to 2000 Nl/l/h. Preferably the reaction conditions are such that, with a given catalyst, the conversion $X_{ii}$ is such that formula I is met. The determination of such reaction conditions belongs to the ordinary skills of those skilled in the art.

The molar synthesis gas usage ratio $F_{ii}$ of this conversion typically lies in the range of from 0.5 to 1.2, in particular from 0.5 to 0.8. The synthesis gas usage ratio for the conversion of synthesis gas to olefinic hydrocarbons is normally significantly lower than the usage ratio for the conversion of synthesis gas to paraffinic hydrocarbons. This is due to the fact that a number of olefin synthesis catalysts also have CO-shift activity, in particular those containing an alkali metal.

Catalysts having CO-shift activity have activity for conversion of carbon monoxide and water to hydrogen gas and carbon dioxide or vice versa. It will be appreciated that water should be present in the reactor to enable a CO-shift to hydrogen gas and carbon dioxide. Water may be injected together with the synthesis gas but is also produced in the olefinic hydrocarbon synthesis process.

In a preferred embodiment of the present invention the second synthesis gas feed is contacted with a catalyst having a CO-shift activity which is more dependent on the reactor temperature than the olefin selectivity of the catalyst in the conversion to olefinic hydrocarbons. This has the advantage that by changing the reactor temperature, the synthesis gas usage ratio can be altered whilst the olefinic hydrocarbon product remains more or less constant. Accordingly, by operating the process at different temperatures, using such catalyst, the conversions $X_i$ and $X_{ii}$ can be altered quite easily whilst still meeting formula I. Preferably, the catalyst comprises a Group VIII metal, in particular iron. Preferably, the catalyst further comprises a Group IIb or VIIb metal, in particular manganese or zinc, optionally in combination with a Group IIb, Vb or VIb metal, in particular vanadium or cerium. More preferably the catalyst further comprises an alkali metal, in particular potassium. Preferably, the K/Fe atomic ratio is in the range of from 0.03 to 0.3 and the (Zn and/or Mn)/Fe atomic ratio is in the range of from 0.3 to 3. The catalyst may or may not contain a carrier. It will be appreciated that the precise variation of usage ratio with temperature depends strongly on the precise catalyst that is employed. However, this relationship can be easily determined by the skilled person by routine experimentation.

In another embodiment of the present invention, the second synthesis gas feed is converted to an oxygenate, preferably an alkanol, as second organic product and another oxygenate, preferably another alkanol, as second by-product. More preferably, the second synthesis gas feed is converted to a mixture of a 2-methyl-1-alkanol, in particular iso-butanol, and methanol as second organic product, and further oxygenates as second by-product.

If the first synthesis gas feed is converted to paraffinic hydrocarbons this second by-product can be used as a blending component with paraffinic hydrocarbons boiling in the gasoline or middle distillate boiling range.

Mixtures of 2-methyl-1-alkanol and methanol can be produced by contacting synthesis gas at synthesis conditions with a catalyst known to those skilled in the art. Examples of suitable catalysts comprise alkali-promoted ZnCr or Cu/ZnO catalysts.

Operating conditions may vary widely and depend on the actual catalyst that is employed. Optimum operating conditions for a specific catalyst can be easily determined by the skilled person by nothing more than routine experimentation. The reaction temperature is typically chosen in the range of from 300 to 500° C., preferably in the range of from 320° C. to 450° C. the total pressure is not critical and may vary from 3 to 50 MPa. Preferably, the pressure is chosen in the range from 9 to 18 MPa. The GHSV is typically selected from 100 to 100000 Nl/l/h, preferably from 1000 to 10000 Nl/l/h.

It will be appreciated that it may also be preferred to prepare other oxygenates like primary alkanols, in particular primary alkanols containing 2–15 carbon atoms in their structure, as second organic product. Catalysts known in the art comprise one or more metals as catalytically active component, chosen from Group VIII, Group Ib and/or Group VIb, in particular iron, nickel, cobalt, copper and/or molybdenum. An overview of various processes to synthesize primary alkanols from synthesis gas has been given by Forzatti et al. in Catal. Rev. Sci. Eng., 33(1&2), 109–168 (1991).

In yet another embodiment of the present invention the first synthesis gas feed is converted to an oxygenate, preferably an alkanol, particularly methanol, as first organic product, and optionally other oxygenates as first by-product. An example of a suitable catalyst comprises copper and zinc on a refractory oxide carrier, in particular an alumina carrier.

Operating conditions may vary widely and depend on the actual catalyst that is employed. Optimum operating conditions for a specific catalyst can be easily determined by the skilled person by nothing more than routine experimentation. The reaction temperature is typically chosen in the range of from 100 to 400° C., preferably in the range of from 240° C. to 280° C. the total pressure is not critical and may vary from 1 to 20 MPa. Preferably, the pressure is chosen in the range from 5 to 10 MPa. The GHSV is typically selected from 100 to 10000 Nl/i/h, preferably from 1000 to 5000 Nl/i/h.

It will be understood that the present invention is not restricted to a process which produces first organic products from only one first synthesis reaction and second organic products from only one second synthesis reaction. Thus the first and second organic products may comprise mixtures of several first and second synthesis reactions. Further, it is of course possible to produce for example paraffinic hydrocarbons as first organic product and produce separately olefinic hydrocarbons and oxygenates as second organic products. It will be appreciated that in such a case the formula $F_{ii}X_{ii}$ in formula I is made up of the sum of two subformula's $F_{ii}X_{ii}$ (olefin) and $F_{ii}X_{ii}$ (oxygenate). Preferably, either one or both organic by-products can be separated and mixed with the first organic product.

In a further embodiment, the present invention relates to a process for the preparation of at least two organic products from a synthesis gas, wherein the synthesis gas, comprising a mixture of carbon monoxide and hydrogen, has a molar ratio of hydrogen to carbon monoxide F, which process comprises effecting in a first stage one of the following procedures:

(a) converting a first synthesis gas feed to paraffinic hydrocarbons or oxygenates, in particular methanol, under conditions of a carbon monoxide conversion of $X_i$ and a molar usage ratio of hydrogen to carbon monoxide of $F_i$, wherein $F_i$ is greater than F; or (b) converting a second synthesis gas feed to olefinic hydrocarbons or oxygenates, in particular mixtures of methanol and iso-butanol, under conditions of a carbon monoxide conversion of $X_{ii}$ and a molar usage ratio of hydrogen to carbon monoxide of $F_{ii}$, wherein $F_{ii}$ is less than F;

and supplying the unconverted carbon monoxide and hydrogen to a second stage in which the other of procedure (a) or (b) is effected; the first and second stages being effected under such conditions that the following relationship is met:

$$F = X_i \cdot F_i + X_{ii} \cdot F_{ii} + c \tag{I}$$

wherein c is up to 0.2, preferably up to 0.1.

An attractive operation is obtained by combining a large scale paraffinic hydrocarbon synthesis unit with a relatively small olefinic hydrocarbon synthesis unit, e.g. one having about ⅓ or ¼ of the production capacity of the paraffinic hydrocarbon synthesis unit. Due to its large scale, e.g. suitably a production capacity at least 20,000 barrels/day, especially at least 50,000 barrels/day, more especially at least 100,000 barrels/day, the paraffinic hydrocarbon synthesis unit will enjoy the advantages of large scale production, and, thus, the paraffinic hydrocarbon produced in the olefinic hydrocarbon synthesis unit will enjoy the same benefits. The olefinic hydrocarbon synthesis unit will produce the olefinic hydrocarbons at a chemically large scale, and have the advantages of relatively low production costs. The amount of paraffinic hydrocarbons produced in an olefinic hydrocarbon synthesis unit is normally between 25 and 60 wt %, suitably about 40wt %. When not combined with a large scale paraffinic hydrocarbon synthesis unit the (fuel) value of the paraffinic hydrocarbons will be relatively low or the paraffinic hydrocarbons have even to be considered as a waste product. Thus, the combination of the two hydrocarbon synthesis units results in synergies in the feed stream as well as in the product streams.

The present invention will now be further described by means of the following Examples.

EXAMPLE I

A typical process scheme in one embodiment of the present invention is as follows. A synthesis gas is prepared by partial oxidation of natural gas at a temperature of 1200° C. in the presence of oxygen at an $O_2/CH_4$ molar ratio of 0.6. The synthesis gas has a hydrogen to carbon monoxide molar ratio of 1.7.

The synthesis gas is mixed with recycle synthesis gas to produce a synthesis gas feed having a hydrogen to carbon monoxide molar ratio of 1.1. The synthesis gas feed is introduced in a heavy paraffin synthesis reactor (HPS reactor) at a GHSV of 800 Nl/l/h. The HPS reactor contains a Fischer-Tropsch catalyst comprising 18 parts by weight of cobalt per 100 pbw of silica carrier. The synthesis gas feed is contacted with the catalyst at a temperature of 220° C. and a pressure of 2.8 MPa. The hydrogen to carbon monoxide usage ratio $F_i$ is 2.1. The process is operated to reach an overall carbon monoxide conversion $X_i$ of 0.75. The process produces the following products (Table I):

TABLE I

| Length of Carbon chain | Paraffins | Olefins (% wt) |
| --- | --- | --- |
| $C_1$ | 5.5 | |
| $C_2$ | 0.4 | 0.1 |
| $C_3$ | 0.5 | 1.5 |
| $C_4$ | 0.5 | 1.5 |
| $C_5$–$C_9$ | 15.0 | ★ |
| $C_{10}+$ | 75.0 | ★ |

★ = not separated

The hydrogen to carbon monoxide molar ratio of synthesis gas leaving the HPS reactor is 0.5. Part of the synthesis gas is recycled (recycle synthesis gas) to produce a first synthesis gas feed to the HPS reactor having a hydrogen to carbon monoxide molar ratio of 1.1.

The $C_2$–$C_4$ olefins are separated from the paraffins by distillation.

The remaining synthesis gas, having a hydrogen to carbon monoxide ratio of 0.5, is used as second synthesis gas feed for an olefinic hydrocarbon synthesis process. The synthesis gas feed is introduced into an olefinic hydrocarbon synthesis reactor (HOS reactor) at a GHSV of 1000 Nl/i/h. The HOS reactor contains an olefin synthesis catalyst comprising iron, potassium, copper and manganese in the following atomic ratio Fe:Mn:K:Cu=100:33:3:1. The catalyst does not contain a carrier. The synthesis gas feed is contacted with the catalyst at a temperature of 270° C. and a pressure of 1.0 MPa. The hydrogen to carbon monoxide usage ratio $F_{ii}$ is 0.5. The process is operated to reach an overall carbon monoxide conversion $X_{ii}$ of 0.25. The process converts 50% of the CO into $CO_2$ and produces the following hydrocarbon products (Table II):

TABLE II

| Lengtn of carbon chain | Paraffins (% wt) | Olefins (% wt) |
| --- | --- | --- |
| $C_1$ | 9.1 | |
| $C_2$ | 1.4 | 6.3 |
| $C_3$ | 2.1 | 9.8 |
| $C_4$ | 2.1 | 7.7 |
| $C_5$–$C_9$ | 16.8 | 25.2 |
| $C_{10}+$ | 9.8 | 9.8 |

The $C_1$–$C_4$ paraffins are separated from the $C_2$–$C_4$ olefins by distillation and combined with $C_1$–$C_4$ paraffins obtained in the first heavy paraffin synthesis process. The $C_5$–$C_9$ paraffins are separated from the $C_5$–$C_9$ olefins by an adsorption process, commercially available from UOP under the trademark "OLEX". the $C_{10}+$ paraffins are separated from the $C_{10}+$ olefins by the same process.

The $C_{10}+$ paraffins from the second step are mixed with the $C_{10}+$ paraffins from the first step and sent to a heavy paraffin conversion unit to convert part of this feed to $C_5$–$C_9$ paraffins. Suitably, $C_5$–$C_9$ paraffins from the HPS reactor, the HOS reactor and the heavy paraffins conversion unit can be combined and used as feed for a thermal cracker (naphtha cracker) to convert the $C_5$–$C_9$ paraffins to $C_2$–$C_4$ olefins.

EXAMPLE II

A typical process scheme in a further embodiment of the present invention is as follows. A synthesis gas is prepared by partial oxidation of natural gas at a temperature of 1200° C. in the presence of oxygen at a $O_2/CH_4$ molar ratio of 0.57. The synthesis gas has a hydrogen to carbon monoxide molar ratio of 1.7.

The synthesis gas is mixed with recycle synthesis gas to produce a synthesis gas feed having a hydrogen to carbon monoxide molar ratio of 1.1. The synthesis gas feed is introduced into a heavy paraffin synthesis reactor (HPS reactor) at a GHSV of 800 Nl/l/h. The HPS reactor contains a Fischer-Tropsch catalyst comprising 18 pbw of cobalt per 100 pbw of silica carrier. The synthesis gas feed is contacted with the catalyst at a temperature of 220° C. and a pressure of 2.8 MPa. The hydrogen to carbon monoxide usage ratio $F_i$ is 2.1. The process is operated to reach an overall carbon monoxide conversion $X_i$ of 0.71. The hydrogen to carbon monoxide molar ratio of synthesis gas leaving the HPS reactor is 0.7. Part of the synthesis gas is recycled (recycle synthesis gas) to produce a first synthesis gas feed to the HPS reactor having a hydrogen to carbon monoxide molar ratio of 1.1.

The remaining synthesis gas, having a hydrogen to carbon monoxide ratio of 0.7, is used as second synthesis gas feed for an alcohol synthesis process. The synthesis gas feed is introduced into an alcohol synthesis reactor (AS reactor) at a GHSV of 3000 Nl/l/h. The AS reactor contains an alcohol synthesis catalyst comprising zinc and chromium in the following atomic ratio Zn:Cr=3.7:1. The catalyst further contains 2.6% by weight of K. The synthesis gas feed is contacted with the catalyst at a temperature of 400° C. and a pressure of 5.0 MPa. The hydrogen to carbon monoxide usage ratio $F_{ii}$ is 0.7. The process is operated to reach a carbon monoxide conversion $X_{ii}$ of 0.29. The process converts 30% by weight of the CO into $CO_2$ and produces as second organic product a mixture of methanol (20% wt) and iso-butanol (20% wt) By-products comprise other oxygenates (30% wt) and hydrocarbons (30% wt). The latter can be mixed with $C_2$–$C_4$ paraffins produced in the HPS reactor. The other oxygenates are separated from methanol and iso-butanol by distillation and are mixed with $C_5$–$C_9$ paraffins or $C_{10}+$ paraffins obtained in the first process which mixture is to be used as gasoline or middle distillate boiling range product. Optionally, the paraffins obtained in the first process may have been subjected to for example a catalytic reforming process prior to admixture with oxygenates from the second process and use of the mixture as gasoline boiling range product. If desired, methanol and isobutanol can be used to produce methyl tertiary-butyl ether (MTBE), which can be used as a blending component for gasoline.

EXAMPLE III

A typical process scheme in another embodiment of the present invention is as follows.

A synthesis gas is prepared by partial oxidation of natural gas as described in Example II.

The synthesis gas is introduced in a heavy paraffin synthesis reactor (HPS reactor, see Example II, using a cobalt/manganese/titania catalyst). The reactor may be operated in a "once-through" way or with a gas recycle. The products from the HPS-reaction are separated into a gaseous fraction (comprising hydrogen, carbon monoxide, methane, $C_2$–$C_4$ paraffins and $C_2$–$C_4$ olefins and inert gases) and a liquid fraction ($C_5+$ compounds).

The gaseous fraction (comprising the unconverted synthesis gas) is introduced into an olefinic hydrocarbon synthesis reactor (HOS reactor, see Example I). The products of the HOS reaction are separated into a gaseous fraction (comprising some unreacted synthesis gas, $C_2$–$C_4$ compounds and inert gases) and a liquid fraction ($C_5+$ compounds).

The liquid fraction of the HOS reaction is separated into a $C_5$–$C_{15}$ fraction, which fraction is then separated into $C_5$–$C_{15}$ olefins and $C_5$–$C_{15}$ paraffins, and a $C_{15}+$ fraction.

The liquid fraction of the HPS reaction, together with the $C_{15}+$ fraction of the HOS reaction are sent to a heavy paraffin conversion unit (HPC) to hydrocrack the compounds in the presence of hydrogen and a suitable catalyst. In addition to hydrocracking, also hydrogenation and hydroisomerization will occur.

The products of the HPC-reaction, together with the $C_5$–$C_{15}$ paraffins fraction from the HOS reaction are separated into a naphtha fraction, a kero fraction, a diesel fraction and a heavy product, requiring three separation units. The heavy fraction is recycled to the HPC reactor.

The carbon monoxide conversion in combination with the molar usage ratio of hydrogen to carbon monoxide in the HPS and the HPC reactor are such that the requirement of formula I is satisfied.

When compared with a stand-alone paraffinic hydrocarbon synthesis unit, the (rather complex) HMU (hydrogen manufacturing unit, necessary to increase the hydrogen/carbon monoxide ratio from 1.7–1.8 to 2.15, the users ratio), which is essentially a non-hydrocarbon producing unit, has been replaced by a hydrocarbon producing unit, producing high value chemical intermediates.

What is claimed is:

1. A process for the preparation of at least two organic products from a synthesis gas by
    (i) converting a first synthesis gas feed to a first organic product selected from paraffinic hydrocarbons and a first by-product;
    (ii) converting a second synthesis gas feed to a second organic product selected from the group consisting of olefinic hydrocarbons and oxygenates and a second by-product;
    (iii) separating the first and/or second by-product from, respectively, the first and/or second organic product, and
    (iv) mixing the separated first by-product with the second organic product or the second by-product with the first organic product, or the first by-product and the second by-product with the second organic product and the first organic product, respectively.

2. The process of claim 1, which comprises
    (iii) separating the first and second by-product from, respectively, the first and second organic product.

3. The process of claim 2, which comprises
    (iv) mixing the first and second by-product with, respectively, the second and first organic product.

4. The process of claim 1 wherein the second organic product is olefinic hydrocarbons and oxygenates.

5. A process for the preparation of at least two organic products from a synthesis gas, wherein the synthesis gas, comprising a mixture of hydrogen and carbon monoxide, has a molar ratio of hydrogen to carbon monoxide F, which process comprises: in a first stage (a) converting a first synthesis gas feed to a first organic product and a first by-product under conditions of a carbon monoxide conversion of $X_i$ and a molar usage ratio of hydrogen to carbon monoxide of $F_i$, wherein $F_i$ is greater than F; or
    (b) converting a second synthesis gas feed to a second organic product and a second by-product under conditions of a carbon monoxide conversion of $X_{ii}$ and a molar usage ratio of hydrogen to carbon monoxide of $F_{ii}$, wherein $F_{ii}$ is less than F;
    and in a second stage (c) supplying the unconverted carbon monoxide and hydrogen to the second stage in which the other of procedure (a) or (b) is effected;
    wherein said first and second stages being effected under such conditions that the following relationship is met:

$$F = X_i \cdot F_i + X_{ii} \cdot F_{ii} + c \qquad (I)$$

wherein c is up to 0.2.

6. The process of claim 5, wherein the first synthesis gas feed is converted to paraffinic hydrocarbons as first organic product and oxygenates and/or olefinic hydrocarbons as first by-product.

7. The process of claim 6, wherein the second synthesis gas feed is converted to olefinic hydrocarbons as second organic product and oxygenates and/or paraffinic hydrocarbons as second by-product.

8. The process of claim 5, wherein the second synthesis gas feed is converted to an oxygenate as second organic product and another oxygenate as second by-product.

9. The process of claim 8, wherein the first synthesis gas feed is converted to an oxygenate as first organic product.

10. A process for the preparation of at least two organic products from a synthesis gas, wherein the synthesis gas, comprising a mixture of carbon monoxide and hydrogen, has a molar ratio of hydrogen to carbon monoxide F, which process comprises: in a first stage (a) converting a first synthesis gas feed to paraffinic hydrocarbons or oxygenates under conditions of a carbon monoxide conversion of $X_i$ and a molar usage ratio of hydrogen to carbon monoxide of $F_i$, wherein $F_i$ is greater than F; or
    (b) converting a second synthesis gas feed to olefinic hydrocarbons or oxygenates under conditions of a carbon monoxide conversion of $X_{ii}$ and a molar usage ratio of hydrogen to carbon monoxide of $F_{ii}$, wherein $F_{ii}$ is less than F;
    and in a second stage (c) supplying the unconverted carbon monoxide and hydrogen to the second stage in which the other of procedure (a) or (b) is effected;
    wherein said first and second stages being effected under such conditions that the following relationship is met:

$$F = X_i \cdot F_i + X_{ii} \cdot F_{ii} + c \qquad (I)$$

wherein c is up to 0.2.

11. The process of claim 10 wherein the first synthesis gas feed is converted to methanol.

12. The process of claim 10 wherein the second synthesis gas feed is converted to a mixture of methanol and isobutanol.

13. The process of claim 1 wherein the second organic product is olefinic hydrocarbons and the second by-product is oxygenates and/or paraffinic hydrocarbons.

14. The process of claim 1 wherein the oxygenates are selected from the group consisting of alkanols, aldehydes and ketones.

15. A process for the preparation of at least two organic products from a synthesis gas by
    (i) converting a first synthesis gas feed to a first organic product selected from olefinic hydrocarbons and a first by-product;
    (ii) converting a second synthesis gas feed to a second organic product selected from the group consisting of paraffinic hydrocarbons and oxygenates and a second by-product;
    (iii) separating the first and/or second by-product from, respectively, the first and/or second organic product, and (iv) mixing the separated first by-product with the second organic product, or the separated second by-product with the first organic product, or the separated first by-product and the separated second by-product with the second organic product and the first organic product, respectively.

16. The process of claim 15, which comprises (iii) separating the first and second by-product from, respectively, the first and second organic product.

17. The process of claim 16, which comprises (iv) mixing the first and second by-product with, respectively, the second and first organic product.

18. The process of claim 15 wherein the second organic product is oxygenates.

19. The process of claim 18 wherein the second by-product is another oxygenate.

20. The process of claim 1 wherein the second organic product is an oxygenate and the second by-product is another oxygenate.

* * * * *